| United States Patent [19] | [11] Patent Number: 4,684,645 |
| Chang et al. | [45] Date of Patent: Aug. 4, 1987 |

[54] BENZOFUSED LACTAMS AS CHOLECYSTOKININ ANTAGONISTS

[75] Inventors: Raymond S. L. Chang, Edison; William H. Parsons, Rahway, both of N.J.

[73] Assignee: Merck & Co., Inc., Rahway, N.J.

[21] Appl. No.: 799,049

[22] Filed: Nov. 18, 1985

Related U.S. Application Data

[63] Continuation of Ser. No. 624,848, Jun. 26, 1984, abandoned.

[51] Int. Cl.[4] .................... A61K 31/55; A61K 31/47; A61K 31/395

[52] U.S. Cl. .................. 514/213; 514/312; 546/157; 540/461; 540/523

[58] Field of Search ................ 260/239.3 B; 546/157; 514/213, 312

[56] References Cited

U.S. PATENT DOCUMENTS 4,410,520 10/1983 Watthey ............... 260/239.3 B
4,537,885 8/1985 Watthey ............... 260/239.3 B

*Primary Examiner*—Robert T. Bond
*Attorney, Agent, or Firm*—Samuel B. Abrams; Salvatore C. Mitri; Hesna J. Pfeiffer

[57] ABSTRACT

Benzofused lactams and their use as antagonists of cholecystokinin are disclosed.

3 Claims, No Drawings

BENZOFUSED LACTAMS AS CHOLECYSTOKININ ANTAGONISTS

This is a continuation of application Ser. No. 624,848, filed June 26, 1984, now abandoned.

BACKGROUND OF THE INVENTION

Cholecystokinin (CCK) is a neuropeptide composed of thirty-three aminoacids. [See: Mutt and Jorpes, *Biochem. J.* 125 678 (1971)]. The carboxyl terminal octapeptide (CCK-8) also occurs naturally and is fully active. CCK exists in both gastrointestinal tissue and the central nervous system. [V. Mutt, *Gastrointestinal Hormones*, G. B. J. Glass, Ed., Raven Press, N.Y., (1980) p. 169.] CCK is believed to play an important role in appetite regulation and CCK may be a physiological satiety hormone. [G. P. Smith, *Eating and Its Disorders*, A. J. Stunkard and E. Stellar, Eds, Raven Press, New York, 1984, p. 67.]

Among additional effects of CCK are stimulation of colonic motility, stimulation of gall bladder contraction, stimulation of pancreatic enzyme secretion, and inhibition of gastric emptying. CCK reportedly co-exists with dopamine in certain mid-brain neurons and thus may also play a role in the functioning of dopaminergic systems in the brain as well as serving as a neurotransmitter in its own right. [See: A. J. Prange et al., "Peptides in the Central Nervous System", *Ann. Repts. Med. Chem.* 17 31, 33 (1982) and references cited therein; J. A. Williams, *Biomed. Res.* 3 107 (1982); and J. E. Morley, *Life Sci.* 30, 479 (1982).]

CCK antagonists are useful in the treatment and prevention of CCK-related disorders of the gastrointestinal, central nervous and appetite regulatory systems of animals, especially humans. Three distinct chemical classes of CCK receptor antagonists have been reported. One class comprises derivatives of cyclic nucleotides; detailed structure-function studies have demonstrated that of the various members of this class, butyryl cyclic GMP, is the most potent. [See: N. Barlos et al., *Am. J. Physiol.*, 242, G161 (1982) and P. Robberecht et al., *Mol., Pharmacol.*, 17, 268 (1980).] The second class comprises peptide antagonists which are C-terminal fragments and analogs of CCK. Recent structure-function studies have shown that both shorter C-terminal fragments of CCK (Boc-Met-Asp-Phe-NH$_2$, Met-Asp-Phe-NH$_2$) as well as longer CCK fragments (CBz-Tyr(-SO$_3$H)-Met-Gly-Trp-Met-Asp-NH$_2$) can function as CCK antagonists. [See: R. T. Jensen et al., *Biochim. Biophys. Acta.*, 757, 250 (1983) and M. Spanarkel et al., *J. Biol. Chem.*, 258, 6746 (1983).] The third class of CCK receptor antagonists comprises the amino acid derivatives; proglumide, a derivative of glutaramic acid and the N-acyl tryptophans including para-chlorobenzoyl-L-tryptophan (benzotript). [See W. F. Hahne et al., *Proc. Natl. Acad. Sci. U.S.A.*, 78, 6304 (1981) and R. T. Jensen et al., *Biochem. Biophys. Acta.*, 761, 269 (1983).] All of these compounds are relatively weak antagonists of CCK (IC$_{50}$:10$^{-4}$–10$^{-6}$M).

SUMMARY OF THE INVENTION

It has now been found that the benzofused lactam compounds of this invention are antagonists of cholecystokinin (CCK). These CCK antagonists are useful in the treatment and prevention of CCK-related disorders of the gastrointestinal, central nervous and appetite regulatory systems of mammals, especially humans.

DETAILED DESCRIPTION OF THE INVENTION

An embodiment of the invention is a class of benzofused lactam compounds having the formula:

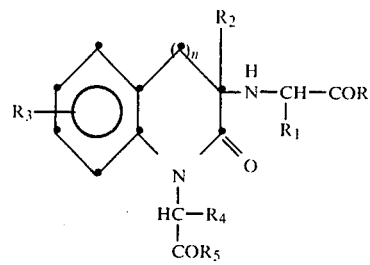

and pharmaceutically acceptable salts thereof wherein
n is 1, 2 or 3,
R$_4$ is hydrogen, lower alkyl, aryl;
R$_2$ is hydrogen,
R$_3$ is H, halo, lower alkyl, or loweralkoxy,
R$_1$ is
  hydrogen;
  alkyl of from 1 to 12 carbon atoms which include branched, cyclic and unsaturated alkyl groups;
  substituted loweralkyl wherein the substituent can be halo, hydroxy, carboxy, carboxamido, loweralkylthio, loweralkoxy, loweralkoxycarbonyl, loweraralkoxycarbonyl, amino, loweralkylamino, lowerdialkylamino, acylamino, carbonyl;
  substituted loweralkylamino wherein the substituent can be halo, hydroxy, alkoxy or cyano; arloweralkylamino; aryloxy; arylthio; aralkyloxy; aralkylthio; benzofused cycloalkyl or bicycloalkyl of from 8–12 carbon atoms;
  aryl or heteroaryl which may be mono-, di- or tri-substituted by loweralkyl, hydroxy, loweralkoxy, halo, amino, acylamino, loweralkylthio or aminoloweralkyl;
  benzofused cycloalkyl or bicycloalkyl of from 8 to 12 carbon atoms;
  arloweralkyl; arloweralkenyl; heteroloweralkyl and heteroloweralkenyl in which the aryl or heteroaryl rings may be mono-, di- or tri-substituted by halo, loweralkyl, hydroxy, loweralkoxy, amino, loweralkylamino, diloweralkylamino, aminoloweralkyl, acylamino, carboxy, haloloweralkyl, nitro, cyano or sulfonamido;
  aralkyl or heteroaralkyl which include branched loweralkyl groups;
  substituted aralkyl or substituted heteroaralkyl which include branched loweralkyl groups wherein the loweralkyl groups can be substituted by amino, acylamino, or hydroxyl and the aryl and heteroaryl groups can be substituted by halo, dihalo, loweralkyl, hydroxy, loweralkoxy, aryloxy, aroyl, arylthio, amino, aminoloweralkyl, loweralkanoylamino, aroylamino, lowerdialkylamino, loweralkylamino, hydroxy, hydroxyloweralkyl, trihaloloweralkyl, nitro, cyano, or sulfonamido;
  any of the arloweralkyl or alkenyl and heteroloweralkyl or alkenyl groups described above in which the aryl or heteroaryl ring is partially or completely hydrogenated; substituted loweralkyl having the formula R$_A{}^1$(CH$_2$)$_n$—Q—(CH$_2$)$_m$ wheren n is 0–2, m is 1–3, R$_A{}^1$ is aryl or heteroaryl optionally substituted by amino, lowerdialkylamino, loweralkylamino, hydroxy, hydroxyloweralkyl, aminoloweralkyl, trihaloloweralkyl, cyano, nitro, sulfonamido, aroyl, loweralkyl, halo, dihalo, and loweralkoxy, and Q is O, is S, SO, $SO_2$, $N-R_B{}^1$, $CONR_C{}^1$, $NR_C{}^1CO$, $CH=CH$ wherein $R_B{}^1$ is hydrogen, loweralkyl, aryl, aralkyl, loweralkanoyl, or aroyl, and $R_C{}^1$ is hydrogen, or loweralkyl;

$R_5$ is
—$OR_6$ or —$NR_7R_8$ wherein $R_6$, $R_7$ and $R_8$ can each independently be hydrogen;
lower alkyl;
substituted lower alkyl wherein the substituents are monohydroxy, dihydroxy or acylamino;
acylloweralkyl;
arloweralkyl;
carboxyloweralkyl;
carboxamidoloweralkyl;
aryl of $C_6$ or $C_{10}$;
heteroaryl, heteroarylalkyl and arylheteroalkyl wherein the aryl groups are $C_5$ to $C_{10}$ and the heteroatoms are O, N or S;
the pharmaceutically acceptable salts thereof.

Pharmaceutically acceptable salts are salts of Formula I with various inorganic and organic acids and bases. Such salts include ammonium salts, alkali metal salts like sodium and potassium salts, alkaline earth metal salts like the calcium and magnesium salts, salts with organic bases, e.g., dicyclohexylamine salts, N-methyl-D-glucamine, salts with amino acids like arginine, lysine and the like, also salts with organic and inorganic acids such as HCl, HBr, $H_2SO_4$, $H_3PO_4$, methanesulfonic, oxalic, pamoic, isethionic, toluenesulfonic, maleic, fumaric, camphorsulfonic, acetic or pivalic acids and the like.

The salts may be prepared by conventional means, e.g., by reacting the free acid or free base forms of formula I with one or more equivalents of the appropriate base or acid in a suitable solvent or medium in which the salt is insoluble or in a solvent or medium in which the salt is insoluble, or in a solvent such as water which is then removed in vacuo or by freeze-drying or by exchanging the ions of an existing salt for another ion on a suitable ion exchange resin.

The alkyl substituents recited above denote straight and branched chain hydrocarbons of $C_1-C_{12}$ such as methyl, hexyl, propyl, dodecyl isopentyl, isopropyl, nopentyl, etc.

Loweralkyl denotes alkyl groups of $C_1$ to $C_8$ such as ethyl, isobutyl, 4-methylpentyl, and the like.

Alkenyl and alkynyl denote unsaturated hydrocarbon groups which are modified so that each contains a carbon to carbon double bond or triple bond, respectively, such as vinyl, 2-butenyl and 1-hexynyl.

Cycloalkyl denotes rings composed of 5 to 8 methylene groups, each which may be substituted or unsubstituted with other hydrocarbon substituents, and include, for example, cyclopentyl, cycloheptyl, 4-methyl cyclohexyl, and the like.

Benzofused cycloalkyl groups denote a cycloalkyl ring of 5 to 8 carbon atoms to which is fused a benzene ring such as indanyl or tetralyl groups.

Bicycloalkyl denotes two cycloalkyl rings of 5 to 8 carbon atoms each joined together in any allowable way s h as perhydroindane, octahydronaphthalene, bicyclo 3:1:3 octane and spiro 4:0:4 nonane.

The loweralkoxy substituent represents a loweralkyl group as described above attached through an oxygen bridge.

The aralkyl and heteroaralkyl substituents recited above represent aryl or heteroaryl groups as herein defined attached through a straight or branched chain hydrocarbon of from one to six carbon atoms, for example, benzyl, phenethyl, 3,3-diphenylpropyl, 3-indolylmethyl, and the like.

Halo means chloro, bromo, iodo, or fluoro.

The aryl substituents are unsubstituted aromatic rings such as phenyl, naphthyl, or biphenyl.

The heteroaryl substituent recited above represents any 5- or 6-membered aromatic ring containing from one to three heteroatoms selected from the group consisting of nitrogen, oxygen, and sulfur, for example, pyridyl, thienyl, furyl, imidazolyl, and thiazolyl; as well as any bicyclic group in which any of the above heterocyclic rings is fused to another aromatic ring, for example, indolyl, quinolinyl, isoquinolinyl, benzimidazolyl, benzothiazolyl, benzthienyl, and naphthyridyl.

The acylamino substituent represents loweralkanoylamino and aroylamino.

Preferred Formula I compounds are those where
n is 1, 2 or 3,
$R_5$ is —$OR_6$ or —$NR_7R_8$ wherein $R_6$, $R_7$ and $R_8$ are independently selected from hydrogen; lower alkyl, aryl, and arloweralkyl;
$R_2$ is
hydrogen;
carboxyloweralkyl;
carboxamidoloweralkyl;
$R_1$ is as defined above;
$R_4$ is hydrogen, lower alkyl, aryl; and
$R_3$ is H, halo, lower alkyl, or lower alkoxy.

More preferred compounds of Formula I are those where
n is 1, 2 or 3,
$R_5$ is —$OR_6$ or —$NR_7R_8$ wherein $R_6$, $R_7$ and $R_8$ are independently selected from hydrogen, lower alkyl, aryl, and arloweralkyl;
$R_4$ is hydrogen, lower alkyl, carboxyloweralkyl, carboxamidoloweralkyl;
$R_2$ is hydrogen;
$R_1$ is as defined above in the preferred group;
$R_3$ is H, halo, lower alkyl, lower alkoxy, or aryl.

Most preferred compounds of Formula I are those where
n is 1, 2 or 3,
$R_4$ is hydrogen, or lower alkyl;
$R_1$ is as defined above in the preferred group;
$R_2$ is hydrogen,
$R_5$ is —$OR_6$ or —$NR_7R_8$ wherein $R_6$, $R_7$ and $R_8$ are independently selected from hydrogen, lower alkyl, benzyl, carboxyloweralkyl, carboxamidoloweralkyl; and,
$R_3$ is H, halo, lower alkyl or lower alkoxy.

A preferred value of n in the above described subgenera is 3 or 2, and more preferably 2.

The preferred, more preferred and most preferred compounds of Formula I also include t pharmaceutically acceptable salts thereof.

The pharmaceutically acceptable salts are salts of Formula I compounds with various inorganic and organic acids and bases. Such salts include ammonium salts, alkali metal salts like sodium and potassium salts, alkaline earth metal salts like the calcium and magnesium salts, salts with organic bases, e.g., dicyclohexylamine salts, N-methyl-Dglucamine, salts with amino acids like arginine, lysine and the like, and salts with organic and inorganic acids; e.g., HCl, HBr, $H_2SO_4$, $H_3PO_4$, methanesulfonic, isethionic, pivalic, oxalic, toluenesulfonic, maleic, fumaric, camphorsulfonic acids and the like.

The salts may be prepared by conventional means, e.g., reacting the free acid or free base form of the product with one or more equivalents of the appropriate base or acid in an appropriate solvent or reaction medium.

An embodiment of this invention is the preparation of compounds of Formula I.

Another embodiment is the use of the compounds of Formula I for the treatment and the prevention of disorders of the gastrointestinal, central nervous, and appetite regulatory systems of mammals, especially of man. Specifically, the Formula I compounds are useful in treatment and prevention of disorders of gastric acid secretion, gastrointestinal motility, pancreatic secretions, and dopaminergic functions. The compounds of Formula I are especially useful in the prevention and treatment of irritable bowel syndrome.

A further embodiment is a composition comprising an effective amount of a compound of Formula I and a pharmaceutically acceptable carrier.

The ability of the compounds of Formula I to antagonize CCK makes these compounds useful as pharmaceutical agents. These compounds will be especially useful in the treatment and prevention of disease states wherein CCK may be involved, for example, gastrointestinal disorders such as irritable bowel syndrome, ulcers, excess pancreatic or gastric secretion, acute pancreatitis, motility disorders, central nervous system disorders caused by CCK's interaction with dopamine such as neuroleptic disorders, tardive dyskinesia, Parkinson's disease, psychosis or Gilles de la Tourette Syndrome, and disorders of appetite regulatory systems.

The compounds of Formula I or pharmaceutically acceptable salts thereof, can be administered to a human subject either alone, or preferably, in combination with pharmaceutically acceptable carriers or diluents, in a pharmaceutical composition, according to standard pharmaceutical practice. Thus, the compositions of the invention can contain other conventional pharmaceutically acceptable compounding ingredients, as necessary or desired. Conventional procedures for preparing such compositions in appropriate dosage forms can be utilized. Whatever the dosage form, it will contain a pharmaceutically effective amount of the present composition.

The present compositions can be administered orally or other than orally; e.g., parenterally, by insufflation, topically, rectally, etc.; using appropriate dosage forms; e.g., tablets, capsules, suspensions, solutions, and the like, for oral administration; suspension emulsions, and the like, for parenteral administration; solutions for intravenous administration; and ointments, transdermal patches, and the like, for topical administration.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be for example, (1) inert diluents such as calcium carbonate, sodium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be (1) suspending agents such as sodium carboxymethylcellulose, methylcellulose, hydroxypropylmethylcellulose, sodium alginate, polyvinylpyrrolidone, gum tragacanth and gum acacia;

(2) dispersing or wetting agents which may be
  (a) a naturally-occurring phosphatide such as lecithin,
  (b) a condensation product of an alkylene oxide with a fatty acid, for example, polyoxyethylene stearate,
  (c) a condensation product of ethylene oxide with a long chain aliphatic alcohol, for example, heptadecaethyleneoxycetano
  (d) a condensation product of ethylene oxide with a partial ester derived from a fatty acid and a hexitol such as polyoxyethylene sorbitol monooleate, or
  (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturallyoccurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

A composition of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compositions of the invention are employed.

When a compound of Formula I or a salt thereof is used as an antagonist of CCK in a human subject, the daily dosage will normally be determined by the prescribing physician. Moreover, the dosage will vary according to the age, weight, and response of the individual patient, as well as the severity of the patient's symptoms. However, in most instances, an effective daily dosage will be in the range from about 0.5 mg to about 1000 mg/kg and preferably 5 mg to about 500 mg/kg in a single or divided doses. On the other hand, it may be necessary to use dosages outside these limits in some cases.

Therefore, it should be understood that the specific dose level for any particular patient will depend upon a variety of factors including the activity of the specific compound exployed, the age, body weight, general health, sex, diet, time of administration, route of administration, rate of excretion, drug combination and the severity of the particular disease undergoing therapy.

In Vitro Activity of Formula I

The biological activity of the compounds of Formula I have been evaluated using an $^{125}$I-CCK receptor binding assay and in vitro isolated tissue preparations.

Materials and Methods

1. CCK Receptor Binding (Pancreas)

CCK-33 was radiolabeled with $^{125}$I-Bolton Hunter reagent (2000 Ci/mmole) as described by Sankara et al. (*J. Biol. Chem.* 254: 9349–9351, 1979). Receptor binding was performed according to Innis and Snyder (*Proc. Natl. Acad. Sci.* 77: 6917–6921, 1980) with the minor modification of adding the additional protease inhibitors, phenylmethane sulfonyl fluoride and o-phenanthroline. The latter two compounds have no effect on the $^{125}$I-CCK receptor binding assay.

Male Sprague-Dawley rats (200–350 g) were sacrificed by decapitation. The whole pancreas was dissected free of fat tissue and was homogenized in 20 volumes of ice-cold 50 mM, Tris HCl (pH 7.7 at 25° C.) with a Brinkmann Polytron PT 10. The homogenates were centrifuged at 48,000 g for 10 min. Pellets were resuspended in Tris Buffer, centrifuged as above and resuspended n 200 volumes of binding assay buffer (50 mM Tris HCl, pH 7.7 at 25° C., 5 mM dithiothriethel, 0.1 mM bacitracin, 1.2 mM phenylmethane sulfonyl fluoride and 0.5 mM o-phenanthroline). For the binding assay, 25 μl of buffer (for total binding) or unlabeled CCK-8 sulfate to give a final concentration of 1μM (for nonspecific binding) or the compounds of Formula I (for determination inhibition of $^{125}$I-CCK binding) and 25 μl of $^{125}$I-CCK-33 (30,000–40,000 cpm) were added to 450 μl of the membrane suspensions in microfuge tubes. All assays were run in duplicate or triplicate. The reaction mixtures were incubated at 37° C. for 30 minutes and centrifuged in a Beckman Microfuge (4 minutes) immediately after adding 1 ml of ice-cold incubation buffer. The supernatant was aspirated and discarded, pellets were counted with a Beckman gamma 5000.

2. CCK Receptor Binding (Brain)

CCK-33 was radiolabeled and the binding was performed according to the description for the pancreas method with modifications according to Saito, et al. (*J. Neurochem,* 37, 483–490 (1981)).

Male Hartley guinea pigs (300–500 g) were sacrificed by decapitation and the brains were removed and placed in ice-cold 50 mM, Tris HCl plus 7.58 g/l Tritma-7.4 (pH 7.4 at 25° C.) Cerebral cortex was dissected and used as a receptor source. Each gram of fresh guinea pig brain tissue was homogenated in 10 ml of Tris/Trizma buffer with a Brinkman polytron PT-10. The homogenates were centrifuged at 42,000 g for 15 min. Pellets were resuspended in Tri Buffer, centrifuged as above and resuspended in 200 volumes of binding assay buffer (10 mM HEPES, pH 7.7 at 25° C., 5 mM MgCl$_2$, 1 mM EGTA, 0.4% BSA (bovine serum albumin), 0.25 mg/ml bacitracin). For the binding assay, 25 μl of buffer (for total binding) or unlabeled CCK-8 sulfate to give a final concentration of 1 μM (for nonspecific binding) or the compounds of Formula I (for determination inhibition of $^{125}$I-CCK binding) and 25 μl of $^{125}$I-CCK-33 (30,000–40,000 cpm) were added to 450 μl of the membrane suspensions in microfuge tubes. All assays were run in duplicate or triplicate. The reaction mixtures were incubated at 25° C. for 2 hours and centrifuged in a Beckman Microfuge (4 minutes) immediately after adding 1 ml of ice-cold incubation buffer. The supernatant was aspirated and discarded, pellets were counted with a Beckman gamma 5000.

3. Isolated guinea pig gall bladder

Male Hartley guinea pigs (400-600 g) were sacrificed by decapitation. The whole gall bladder was dissected free from adjacent tissues and cut into two equal halves. The gall bladder strips were suspended along the axis of bile duct in 5 ml organ bath under 1 g tension. The organ bath contained a Kreb's bicarbonate solution (NaCl 118 mM, KCl 4.75 mM, CaCl 2.54 mM, $KH_2PO_4$ 1.19 mM, Mg $SO_4$ 1.2 mM, $NaHCO_3$ 25 mM and dextrose 11 mM) maintained at 32° C. and bubbled with 95% $O_2$ and 5% $CO_2$. Isometric contractions were recorded using Statham (60 g; 0.12 mm) strain gauges and a Hewlett-Packard (77588) recorder. The tissues were washed every 10 minutes for 1 hr to obtain equilibrium prior to the beginning of the study. CCK-8 was added cumulatively to the baths and $EC_{50}$'s determined using egression analysis. After washout (every 10 minutes for 1 hr), the compound of Formula I was added at least 5 minutes before the addition of CCK-8 and the $EC_{50}$ of CCK-8 in the presence of the compound of Formula I similarly determined.

4. Isolated longitudinal muscle of guinea pig ileum

Longitudinal muscle strips with attached nerve plexus were prepared as described previously (*Brit J. Pharmac.* 23: 356-363, 1964; *J. Physiol.* 194: 13-33, 1969). Male Hartley guinea pigs were decapitated and the ileum was removed (10 cm of the terminal ileum was discarded and the adjacent 20 cm piece was used). A piece (10 cm) of the ileum was stretched on a glass pipette. Using a cotton applicator to stroke tangently away from the mesentery attachment at one end, the longitudinal muscle was separated from the underlying circular muscle. The longitudinal muscle was then tied to a thread and by gently pulling, stripped away from the entire muscle. A piece of approximately 2 cm was suspended in 5 ml organ bath containing Krebs solution and bubbled with 95% $O_2$ and 5% $CO_2$ at 37° C. under 0.5 g tension. CCK-8 was added cumulatively to the baths and $EC_{50}$ values in the presence and absence of compounds of Formula I determined as described in the gall bladder protocol (above).

In Vitro Results

1. Effect of the Compounds of Formula I on $^{125}$I-CCK-33 Receptor Binding Compounds of Formula I inhibited specific $^{125}$I-CCK-33 binding in a concentration dependent manner with an $IC_{50}$ less than or equal to 100 μM such as for example:

1-t-butoxycarbonylmethyl-3-(1-carboethoxy-3-phenyl-1-propyl)aminohomodihydrocarbostyril, $IC_{50}$=2.4 μM;

1-carbomethoxymethyl-3-(1-carbomethoxy-3-phenyl-1-propyl)aminohomodihydrocarbostyril, $IC_{50}$=10 μM;

1-t-butoxycarbonylmethyl-3-(1-carboethoxy-3-phenyl-1-propyl)aminohexahydrobenzazocine-2-one, $IC_{50}$=3 μM; and 1-t-butoxycarbonylmethyl-3-(1-carboethoxy-3-(3-indolyl)-1-propyl)aminohomodihydrocarbostyril, $IC_{50}$=0.4 μM.

2. Effect of the compounds of Formula I on CCK induced contraction of guinea pig ileum or gall bladder 1-t-butoxycarbonylmethyl-3-(1-carboethoxy-3-(3-indolyl)-1-propyl)aminohomodihydrocarbostyril at 4.2 μM shifted CCK dose response to the right approximately 2.6 fold without affecting maximal responses in guinea pig ileum. Ethyl-3-[(1-ethoxycarbonyl)-3-phenylpropyl)amino]-2,3.45, tetrahydro-2-oxo-1H-1-benzazepine-1-acetate at 26 μM caused about 10 times shift of CCK dose response in the guinea pig gall bladder without reducing maximal responses. These results indicates that the compounds of Formula I are competitive antagonists of CCK in these tissues.

The compounds of this invention can also be administered in combination with antihypertensives and/or diuretics and/or calcium entry blockers.

Typically, the individual daily dosages for these combinations can range from about one-fifth of the minimally recommended clinical dosages to the maximum recommended levels for the entities when they are given singly.

The compounds of Formula I may be prepared by any convenient process. Useful processes are illustrated by the following reaction equations wherein $R_1$-$R_5$ and n are as defined above unless otherwise indicated.

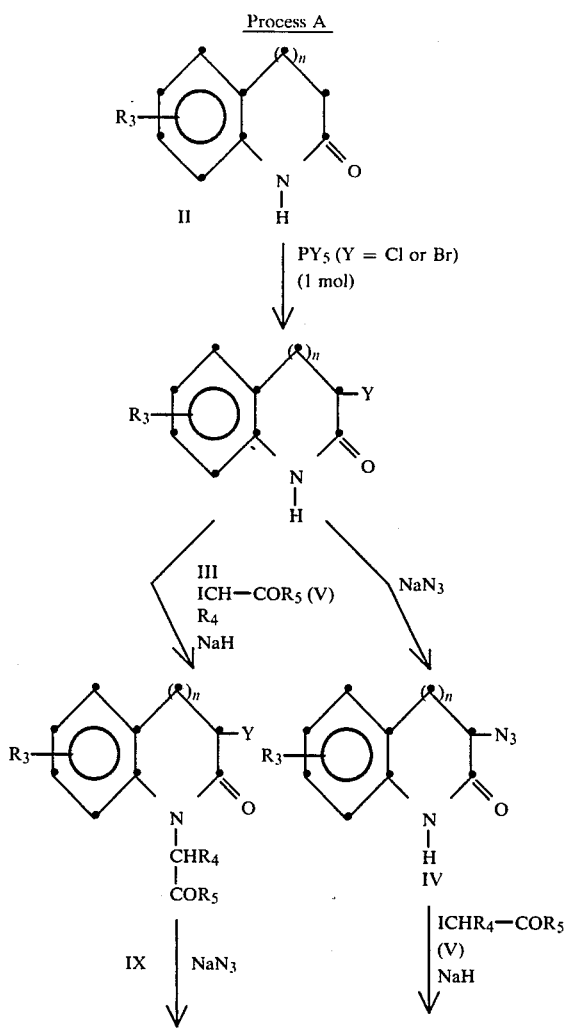

-continued

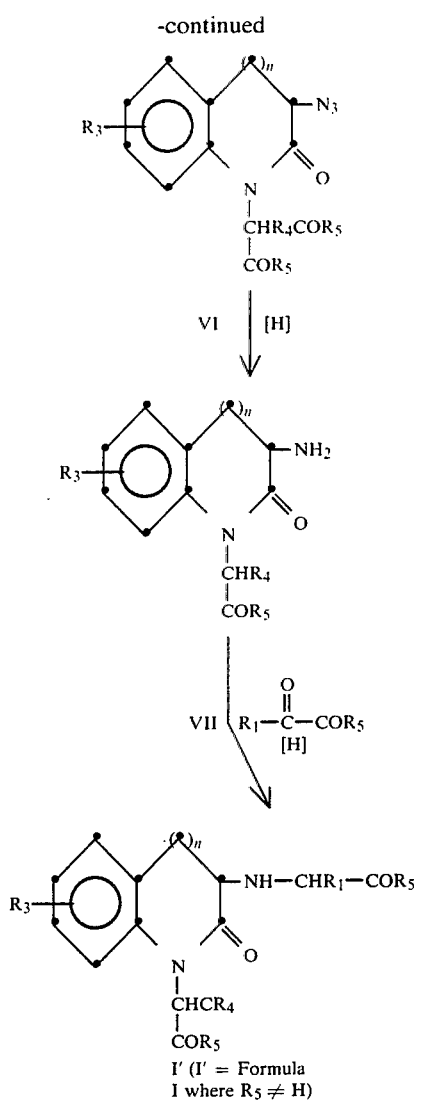

I' (I' = Formula I where $R_5 \neq H$)

Alternate Process for IX

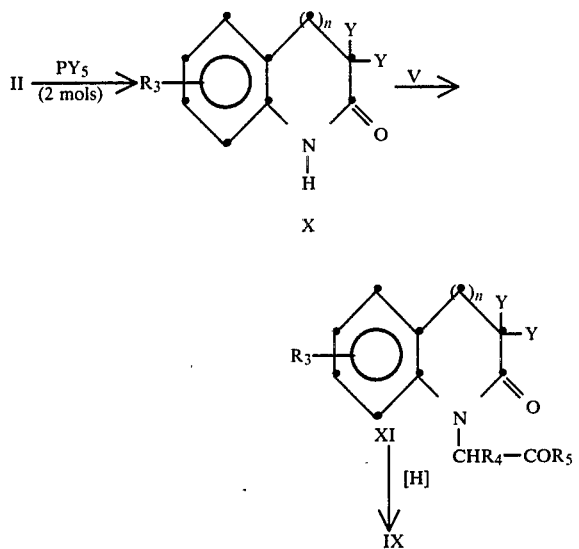

Process B

-continued

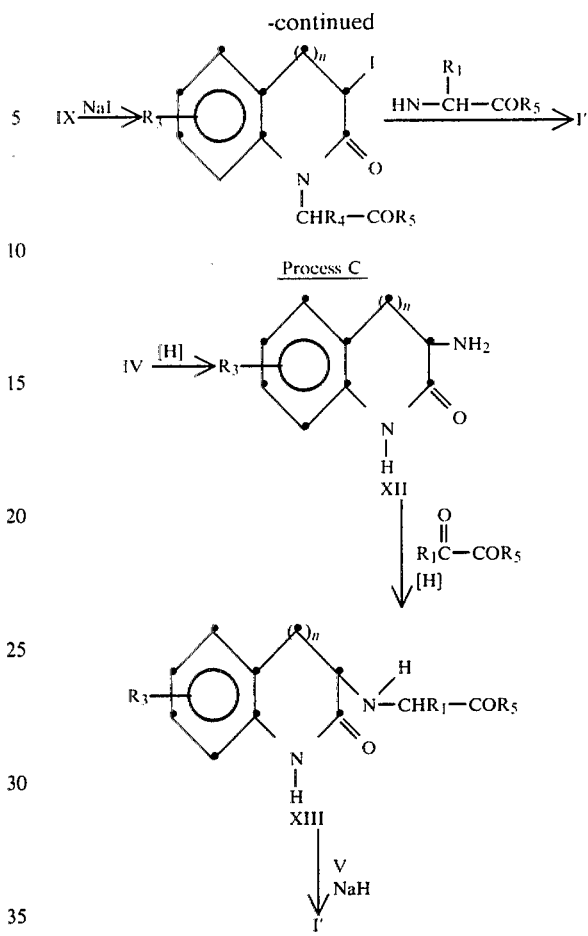

Process C

Process A

Benzofused lactam II ring size ranging from 6 to 8 (n=1,2,3), prepared from a precursor ketone by a procedure of Blicke et al., *J. Am. Chem. Soc.*, 76, 2317 (1954), is converted to (III), with $PX_5$ where X=Br or Cl [Nagasawa et al., *J. Med. Chem.*, 14, 501 (1971)]. Reaction of (III) with sodium or lithium azide in a suitable solvent such as DMF or ethanol [see, for example, Brenner et al., *Helv. Chem. Acta*, 41, 181 (1958)] affords (IV) which can be alkylated with an iodoester (V) in the presence of a strong base, like sodium hydride, in a solvent such as DMF or THF to produce (VI). Reduction of (VI) with hydrogen and a suitable catalyst, such as palladium on carbon, affords (VII). Intermediate (VII) is then reductively coupled with a keto acid or ester (VIII) in a solvent such as ethanol using a catalyst such as palladium on carbon to afford (I') ($R_5 \neq H$). Alternatively, sodium cyanoborohydride can be used to effect the reduction.

Groups $R_5$ may be modified by known methods, if desired. For example, if $R_6$=Et or t-Bu, the diester (I) can be converted to the monoester $R_6$=Et or H by treatment with trifluoroacetic acid. If $R_6$=Et, (I) can be converted to the diacid $R_6$=H by basic hydrolysis.

Alternatively, (III) may be alkylated with (V) in the presence of a strong base, like sodium hydride, and the intermediate (IX) converted to (VI) by reaction with an azide salt as described above.

Alternate Process for IX

If desired, (IX) may be prepared by the alkylation of (X) [prepared from II using the alternate conditions of Nagasawa, above] with (V) to afford intermediate (XI). Treatment of (XI) with hydrogen and a catalyst, such as palladium on carbon, affords (IX).

Process B

Alternatively, IX (Y=Cl, Br; $R_6 \neq OH$) may be converted to the iodo compound IX (X=I) by known methods, for example, sodium iodide in acetone. Reaction of this iodo lactam with an amino acid ester in a solvent such as toluene or DMF in the presence of a halide scavenger such as $Ag_2O$ gives I ($R_6 \neq OH$).

Process C

If desired, IV may be reduced with hydrogen in the presence of a suitable catalyst to afford XII which can be alkylated with a ketoester in the presence of hydrogen on a suitable catalyst to give XIII. Alternatively, sodium cyanoborohydride may be used. Alkylation of XIII to afford I' ($R_6 \neq OH$) can be carried out with an iodoester in the presence of a strong base such as sodium hydride in a solvent such as THF.

In the compound of Formula I, the carbon atoms to which $R_1$, $R_2$ and $R_4$ are attached and the ring carbon atom to which the

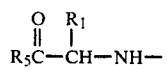

group is attached may be asymmetric. Thus, the compounds of this invention exist in diastereoisomeric forms or in mixtures thereof. The processes described above can utilize racemates, enantiomers or diastereomers as starting materials. When diastereomeric intermediates or products result from the synthetic procedures, the diastereomeric intermediates or products can be separated by chromatographic or fractional crystallization methods. When racemic mixtures result, they may be resolved by crystallization of salts of optically active acids or bases or by other methods known in the art. The part-structures

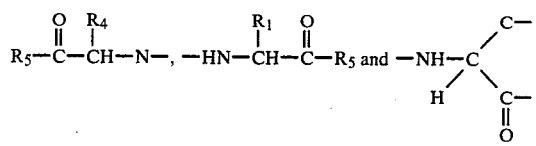

of Formula I can be in two configurations (S or R) and both are within the scope of this invention, although S is generally preferred. Both configurations at the carbon to which $R_2$ is attached are encompassed within this invention.

The following Examples illustrate preparation of representative compounds of Formula I. All temperatures are in ° C.

EXAMPLE 1

A. 1-Butoxycarbonylmethyl-3-aminodihydrocarbostyril

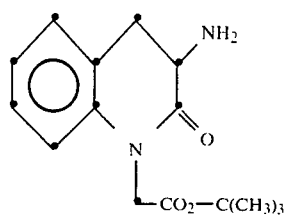

To a suspension of 2.42 gm NaH (50% oil dispersion washed 3×hexanes) in 50 ml of THF at 0° C. was added solid 5 gm (0.025 mol) of 3-aminodihydrocarbostyrilhydrochloride (T. J. McCord, Arch. of Biochem. & Biophys. 102 48 (1963)) stirring at 0° C. until the evolution of hydrogen had ceased at which time the reaction mixture was warmed to room temperature and stirred a further 1 hour. To the stirred reaction mixture was added dropwise a solution of 6 gm of t-butyl iodoacetate in 20 ml of THF stirring a further 2 hours at room temperature at which time the reaction was quenched with 20 ml of saturated $NaHCO_3$. The reaction mixture was diluted with 20 ml of $H_2O$ and extracted 2×50 ml of 9:1 ethylacetate:acetonitrile. The organic layers were combined, filtered through $MgSO_4$ and concentrated in vacuo to give 5 gm of 1-t-butoxycarbonylmethyl-3-aminodihydrocarbostyril.

NMR ($CDCl_3$, TMS): 1.4 (s, 9H); 2.0–3.2 (m, 4H), 3.4–3.8 (m, 1H); 4.6 (Q, 2H); 6.6–7.2 (m, 4H).

IR: C=O 1738, 1680.

B. 1-Carbomethoxymethyl-3-(1-carboethoxy-3-phenyl-1-propyl)aminodihydrocarbostyril (racemate mixture)

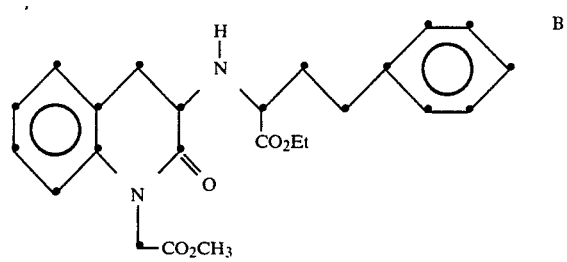

A solution of 2.76 gm (0.010 mol) of 1-t-butoxycarbonylmethyl-3-amino dihydrocarbostyril, 10 gm of ethyl 4-phenyl-2-oxo-butyrate and 0.60 ml of acetic acid in 20 ml of absolute ethanol was stirred 1 hour at room temperature at which time was added dropwise over 8 hours a solution of 1.57 gm of $NaCNBH_3$ in 20 ml of ethanol. After stirring a further 4 hours at room temperature the reaction mixture was concentrated in vacuo. The crude reaction mixture was partitioned between $H_2O$ and ethylacetate. The aqueous layer was extracted 2× with ethylacetate and the combined organic layers filtered through $MgSO_4$ and concentrated at reduced pressure. The reaction mixture was diluted with 20 ml of trifluoroacetic acid and stirred 2 hours at room temperature after which it was concentrated at reduced pressure. The crude mono acid (B where $CH_3$ is H) was taken up in 20 ml of saturated $NaHCO_3$, washed 3×50 ml of ethyl acetate. The aqueous layer was concentrated in vacuo, redissolved in 30 ml of methanol, cooled to 0° C., saturated with HCl gas, sealed, warmed to room temperature and stirred overnight at room temperature. The reaction mixture was subsequently concentrated in vacuo, diluted with saturated $K_2CO_3$ and extracted 3 times with ethyl acetate. The combined organic fractions were filtered through $MgSO_4$ and concentrated at reduced pressure. The crude reaction product B was chromatographed (silica, 2:1 ether:hexanes) and two diastereomeric B racemates were isolated.

Racemate A: 500 mg.

TLC (silica, 2:1 ether:hexanes): $R_f$=0.28.

NMR (CDCl$_3$, TMS) 1.2 (t, 3H): 1.8–2.2 (m, 3H); 2.6–3.1 (m, 6H); 3.2–3.6 (m, 2H); 3.65 (s, 3H); 4.1 (Q, 2H); 4.6 (Q, 2H); 6.8–7.1 (s, 9H).

Racemate B: 1.5 gm.

TLC (silica, 2:1 ether:hexanes): $R_f$=0.20.

NMR (CDCl$_3$, TMS) 1.3 (s, 3H): 1.8–3.2 (m, 8H); 3.4–3.7 (m, 2H); 3.7 (s, 3H); 4.1 (Q, 2H); 4.6 (Q, 2H); 6.8–7.2 (m, 9H).

EXAMPLE 2

1-Carboxymethyl-3-(1-carboxy-3-phenyl-1-propyl)-dihydrocarbostyril

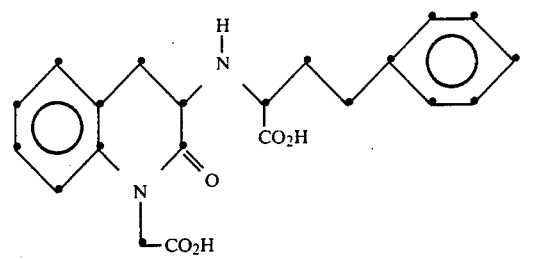

C

Racemate A

A reaction mixture consisting of 900 mg (0.00212 mol) of the diester racemate A of Example 1, 2 ml of methanol and 2.2 ml of a 4N solution of NaOH in H$_2$O was stirred 12 hours at room temperature. Subsequently the reaction mixture was concentrated at reduced pressure. Upon acidification with acetic acid the diacid C precipitated out and was filtered, washed with H$_2$O and dried, giving 600 mg of the diacid C as its mono sodium salt.

TLC (silica, 1:1:1:.5 H$_2$O:nB$_4$OH:EtOAc:HOAc): $R_f$ 0.50.

An. Calc. for C$_{21}$H$_{22}$N$_2$O$_5$Na: 1.5 H$_2$O C, 58.27; H, 5.43; N, 6.47. Found: C, 58.11; H, 5.62; N, 6.02.

EXAMPLE 3

A. 3-Bromo-homodihydrocarbostyril

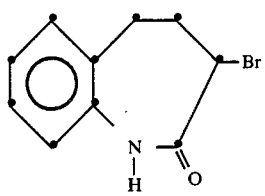

D

To a solution of 15 gm (0.093 mol) of homo dihydrocarbostyril (L. H. Briggs, J.C.S., 456 (1937)) in 200 ml of chloroform was added in increments over a period of an hour 19 gm of PCl$_5$ at which time was added 140 mg of iodine followed by a slow dropwise addition of 90 ml of a 1M solution of bromine in chloroform. The reaction mixture was warmed to room temperature where stirring was continued a further 1 hour.

The crude reaction mixture was concentrated in vacuo and then partitioned between water, ice and chloroform. The aqueous layer was extracted 2 times with methylene chloride and the combined organic fractions were filtered through MgSO$_4$ and concentrated in vacuo. The crude bromide D was chromatographed (silica, 2:1 ether:hexanes) to give 6.5 gm of pure D bromide.

TLC (silica, 2:1 ether:hexanes): $R_f$=0.65.

NMR (CDCl$_3$, TMS): 2.4–3.0 (m, 4H); 4.4–4.7 t, 1H); 7.2 (s, 4H); 9.2 (bs, 1H).

IR: 1650 cm$^{-1}$.

mass spectrum: M$^+$ 239, m/e: 241 (M$^+$, +2); 160 (M$^{+2}$, —Br); 132 (—C=O).

B. 3-Azido homodihydrocarbostyril

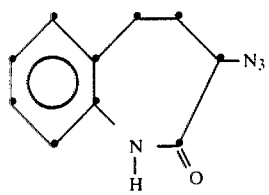

E

To a solution of 9.98 gm (0.0417 mol) of 3-bromo homodihydrocarbostyril in 200 ml of DMF was added 10.8 gm of sodium azide stirring 12 hours at 60° C. at which time the DMF was removed at reduced pressure. To the crude reaction mixture was added 50 ml of water and the mixture was then extracted 3 times with 50 ml of chloroform. The combined organic fractions were combined, washed with 25 ml of a saturated solution of NaCl, filtered through MgSO$_4$ and concentrated at reduced pressure. Chromatography (silica, 2:1 ether:-hexanes) gave 7.92 gm of pure E azide. m.p. 150°–151° C.

TLC (silica, 2:1 ether:hexanes): $R_f$=0.71.

El. An. Calc. for C$_{10}$H$_{10}$N$_4$O. N, 27.71; C, 59.39; H, 4.98. Found: N, 27.27; C, 59.25; H, 4.98.

NMR (CDCl$_3$, TMS): 2.2–2.8 (m, 4H), 3.6–4.0 (dd, 1H); 7.2 (bs, 4H) 9.2 (bs, 1H)IR N$_3$ 2130, CO 1678.

mass spectrum: M$^+$ 202, m/e 174 (M$^+$—N$_2$; 146 (C=O).

C. 1-t-Butoxycarbonylmethyl-3-azido homodihydrocarbostyril

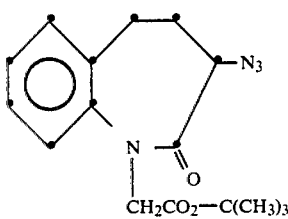

F

To a suspension of 1 gm of sodium hydride (50% dispersion in oil washed 3 times with hexanes) in 20 ml of THF at 0° C. was added dropwise a solution of 4.2 gm (0.02 mol) of 3-azido homodihydro carbostyril and 3 ml of t-butyl iodo acetate in 20 ml of THF. The reaction was carefully monitored by TLC (silica, 2:1 ether:hexanes) until reaction was complete at which time the reaction was quenched with 30 ml of saturated NH4Cl, diluted with 20 ml H2O and extracted 3 times with 50 ml CH2Cl2. The combined organic layers were filtered, concentrated in vacuo and chromatographed (silica, 2:1 ether:hexanes) to give 4.5 gm of pure product F.

m.p.: 103°–104° C.

TLC (silica, 2:1 ether:hexanes): $R_f = 0.74$.

El. An. Calc. for $C_{16}H_{20}N_4O$: N, 17.71; C, 60.74; H, 6.37. Found: N, 17.39; C, 60.54; H, 6.61.

NMR (CDCl3, TMS): 1.5 (s, 9H), 2.2–3.4 (m, 4H); 3.5–4.0 (overlapping doublets, 1H); 4.2–4.8 (ABQ, 2H); 7.2 (s, 4H).

mass spectrum: $M^+$ 316, m/e 288 ($M^+$—$N_2$; 260 ($M^+$—$C_4H_9$).

D. 1-t-Butoxycarbonylmethyl-3-amino homodihydrocarbostyril

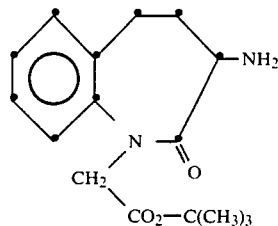

A solution of 8.01 gm of 1-t-butoxycarbonylmethyl-3-azido homo dihydrocarbostyril in 150 ml of absolute ethanol with 0.8 gm of Pd/C 10% was hydrogenated for 12 hr at room temperature and 40 lbs of $H_2$. The reaction was subsequently filtered and the ethanol removed at reduced pressure to give 7.05 gm of pure amine G.

m.p.: 107°–109° C.

El. An. Calc. for $C_{16}H_{22}N_2O_3.\frac{1}{2}H_2O$: N, 9.36; C, 64.19; H, 7.41 Found: N, 9.18; C, 64.17; H, 7.53.

NMR (D2O, CDCl3, TMS): 1.4 (s, 9H), 2.2–3.8 (m, 5H); 4.1–4.7 (ABQ, 2H); 7.05 (bs, 4H).

IR: C=O 1735, 1660.

mass spectrum: $M^+$ 290, m/e 262 ($M^+$—C=O); 234 $M^+$—$C_4H_8$); 217 ($M^+$—$C_4H_9O$).

E. 1-t-Butoxycarbonylmethyl-3-(1-carboethoxy-3-phenyl-1-propyl]-amino homodihydrocarbostyril (Racemate mixture)

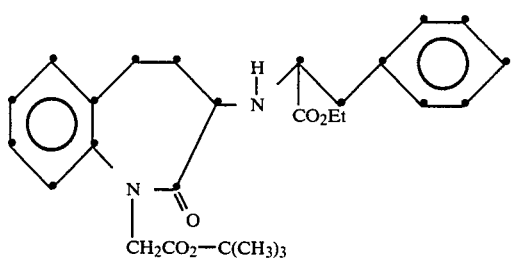

A solution of 1 gm (0.00345 mol) of 1-t-butoxy carbonylmethyl-3-amino homodihydrocarbostyril, 3.5 gm of ethyl 4-phenyl-2-oxobutyrate and 200 μl of acetic acid in 12 ml of absolute ethanol was stirred 1 hour at room temperature. To the stirred solution was added dropwise over a 12 hour period a solution of 545 mg of NaCNBH3 in 12 ml of ethanol. After stirring a further 8 hours the reaction was concentrated at reduced pressure and partitioned between H2O and ethyl acetate. After extracting twice with ethyl acetate the combined organic layers were filtered through MgSO4 and concentrated in vacuo. The crude reaction mixture was chromatographed (silica, 1:1 ether:hexanes) and two diastereomeric H racemates were isolated.

Racemate Diester A: 450 mg.

TLC (silica, 1:1, ether:hexanes): $R_f = 0.31$.

NMR (CDCl3, TMS): 1.1–1.4 (t, 3H), 1.45 (s, 9H), 1.8–3.2 (m, 11H); 3.9–4.3 (Q, 2H); 4.1–4.7 (ABQ, 2H); 7.1–7.3 (m, 9H).

Racemate Diester B: 520 mg.

TLC (silica, 1:1, ether:hexanes) $R_f = 0.23$.

NMR (CDCl3, TMS): 0.9–1.2 (t, 3H), 1.4 (s, 9H); 1.8–3.4 (m, 11H); 3.8–4.2 (Q, 2H); 4.1–4.7 (ABQ, 2H); 7.2 (s, 9H).

EXAMPLE 4

1-Carboxymethyl-3-(1-carboxy-3-phenyl-1-propyl)-aminohomodihydrocarbostyril

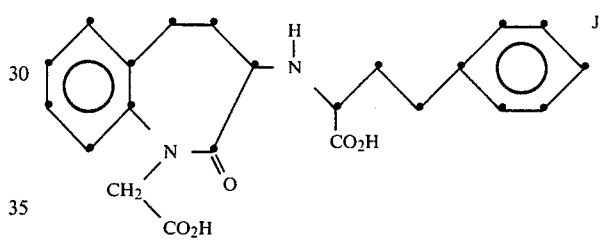

Racemate A 250 mg of racemate iester A of Example 3 was stirred 2 hours with 5 ml of trifluoroacetic acid at which time the reaction mixture was concentrated in vacuo. The crude product in 1 ml of H2O was treated with 600 μl of a 4N NaOH in H2O solution and stirred 7 hours at room temperature. The crude reaction mixture was partially concentrated in vacuo at which time the monosodium salt of J precipitated out. The suspension was filtered, the solid washed with H2O and dried under vacuum to give 125 mg of a diacid monosodium salt of J.

TLC (silica, 1:1:1:.5, H2O:ethylacetate:nBuOH:-HOAc): $R_f = 0.60$.

El. An. Calc. for $C_{22}H_{23}N_2O_5Na.2.5H_2O$: C, 56.90; H, 5.82; N, 6.04. Found: C, 56.84; H, 5.64; N, 5.81.

Racemate B 550 mg of the racemate diester B of Example 3 was converted to the diacid J by the same procedure described above to give 250 mg of free diacid.

TLC (silica, 1:1:1:.5, H2O:ethylacetate:nBuOH:-HOAc): $R_f = 0.67$.

El. An. Calc. for $C_{22}H_{23}N_2O_5.\frac{1}{4}H_2O$: C, 66.02; H, 5.75; N, 7.00. Found: C, 66.04; H, 6.13; N, 6.85.

EXAMPLE 5

1-Carbomethoxymethyl-3-(1-carbomethoxy-3-phenyl-1-propyl)aminohomodihydrocarbostyril

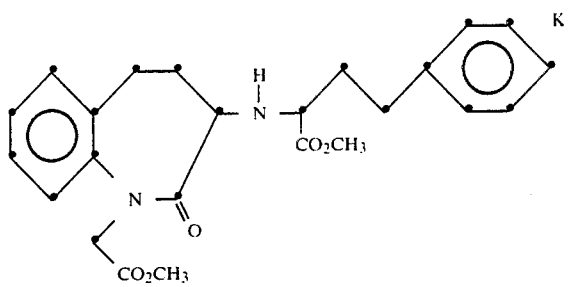

A solution of 1 gm of 1-carboxymethyl-3-(1-carboxy-3-phenyl-1-propyl)amino homodihydrocarbostyril (Racemate B of Example 4) in 20 ml of methanol was cooled to 0° C. and saturated with HCl gas. The reaction mixture was then sealed and stirred overnight at room temperature. The reaction mixture was subsequently concentrated at reduced pressure and partitioned between a saturated aqueous solution of $K_2CO_3$ and ethyl acetate. The aqueous layer was extracted two times with ethyl acetate and the combined organic fractions filtered through $MgSO_4$ and concentrated at reduced pressure. The crude product was chromatographed (silica, 3:1 ether:hexanes) to give 700 mg of pure dimethyl ester K.

TLC (silica, 3:1 ether:hexanes): $R_f=0.56$.

An. Calc. for $C_{24}H_{28}N_2O_5.\frac{1}{4}H_2O$. N, 6.52; C, 67.13; H, 6.52. Found: N, 6.28; C, 67.14; H, 6.60.

NMR (CDCl$_3$, TMS): 1.8–3.4 (m, 11H); 3.5 (s, 3H); 3.7 (s, 3H); 4.2–4.7 (ABQ, 2H); 7.1 (bs, 9H).

EXAMPLE 6

1-Carboxymethyl-3-(1-carboethoxy-3-phenyl-1-propyl)amino homodihydrocarbostyril

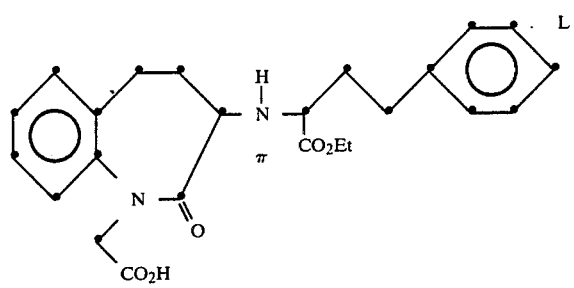

A solution of 550 mg of 1-t-butoxycarbonylmethyl-3-(1-carboethoxy-3-phenyl-1-propyl)amino homodihydrocarbostyril in 10 ml of trifluoroacetic acid was stirred at room temperature for 2 hours. The reaction mixture was concentrated in vacuo, diluted with water and concentrated a second time in vacuo to give a white solid. The solid was triturated with ether and filtered to give 400 mg of the $CF_3CO_2H$ salt of the desired product L.

An. Calc. for $C_{24}H_{28}N_2O_5 \cdot CF_3CO_2H$. H, 5.34; C, 57.51; N, 5.16. Found: H, 5.46; C, 57.68; N, 5.03.

NMR (CD$_3$OD): 1.2 (t, 3H); 2.0–3.0 (m, 9H); 3.6–4.2 (m, 4H); 4.5 (s, 2H); 7.1–7.3 (overlapping singlets, 9H).

EXAMPLE 7

1-Carbobenzyloxymethyl-3-(1-carboxy-3-phenoxy-1-propyl)amino homodihydrocarbostyril

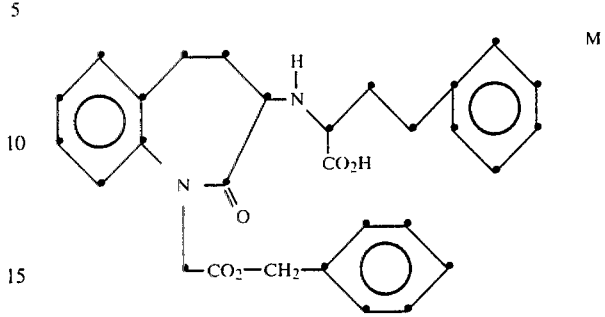

To a suspension of 1.90 gm of NaH (50% in oil washed 3 times with hexanes) in 40 l of THF at room temperature was added dropwise a solution of 6.5 gm of 3-amino homodihydrocarbostyril and 1.56 gm of benzyliodoacetate in 10 ml of THF stirring a further 2 hr at room temperature. The reaction was subsequently quenched with 10 ml of $H_2O$ and extracted two times with ethyl acetate. The combined organic fractions were filtered through $MgSO_4$ and concentrated in vacuo to obtain 1-carbobenzyloxymethyl-3-amino homodihydrocarbostyril.

NMR (CDCl$_3$, TMS): 1.8–3.0 (m, 6H); 3.1–3.4 (m, 1H); 4.6 (ABQ, 2H); 5.1 (s, 2H); 7.0–7.3 (m, 9H).

A solution of 5 gm of 1-carbobenzyloxymethyl-3-amino homodihydrocarbostyril, 16 gm of t-butyl-4-phenyl-2-oxobutyrate and 860 ml of acetic acid in 60 ml of absolute ethanol was stirred 1 hr at room temperature at which time was added dropwise over 18 hours a solution of 2.4 gm of NaCNBH$_3$ in 40 ml ethanol. The reaction mixture was concentrated in vacuo and partitioned between H$_2$O and ethyl acetate. The aqueous layer was extracted 2 times with ethyl acetate and the combined organic layers were filtered through MgSO$_4$ and concentrated in vacuo. The crude reaction mixture was chromatographed (silica 1:1 ether:hexanes) and the first diastereomeric racemate diester was isolated.

NMR (CDCl$_3$, TMS): 1.4 (s, 9H); 1.6–3.2 (m, 11H); 4.5 (ABQ, 2H); 4.6 (s, 2H); 7.0–7.3 (m, 14H).

Said diester in 5 ml of methylene chloride and 5 ml of trifluoro acetic acid was stirred 8 hr at room temperature at which time the reaction was concentrated in vacuo, redissolved in carbon tetrachloride and reconcentrated in vacuo to give 600 mg of monobenzyl ester M.

NMR (CDCl$_3$): 2.0–3.0 (m, 9H); 3.4–3.8 (m, 2H); 4.4 (bs, 2H); 5.0 (s, 2H); 7.0–7.3 (m, 14H).

EXAMPLE 8

A. 3-Bromohexahydrobenzoazocin-2-one

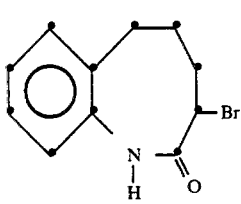

To a solution of 15 gm (0.084 mol) of hexahydrobenzoazocin-2-one (Chemica Scandinavia, 18, 191 (1964))

in 150 ml of chloroform at 0° C. was added 8.8 gm of PCl₅ in increments over a period of an hour. Subsequently, to the reaction mixture was added 70 mg of iodine followed by slow dropwise addition of 84 ml of a 1M solution of bromine in chloroform. The reaction mixture was warmed to room temperature and stirred for 1 hour at which time it was concentrated at reduced pressure. To the crude product was added a mixture of ice and water and the mixture was extracted 3 times with methylene chloride. The combined organic fractions were filtered through MgSO₄ and concentrated at reduced pressure. The solid bromide was recrystallized with a mixture of chloroform and hexanes to give 12 gm of pure product N.

m.p.: 194°–195° C.

TLC (silica, 2:1 ether:hexanes): $R_f=0.36$.

An. Calc. for $C_{11}H_{12}NOBr.\frac{1}{4}H_2O$. N, 5.41; C, 51.08; H, 4.68. Found: N, 5.29; C, 50.75; H, 4.53.

NMR (CDCl₃, TMS): 1.6–2.9 (m, 6H); 4.2–4.5 (bt, 1H); 7.2 (s, 4H); 8.5 (bs, 1H).

mass spectrum: M⁺ 253, m/e: 252 (p+2, 10%); 179 (M⁺—Br); 146 (C=O).

B. 3-Azidohexahydrobenzoazocine-2-one

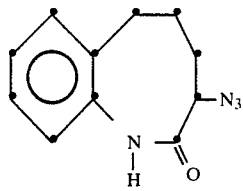

P

To a solution of 10 gm (0.00394 mol) of 3-bromohexahydrobenzoazocine-2-one in 100 ml of dimethylformamide was added 10 gm of sodium azide and the resultant reaction mixture was stirred 12 hours at 60° C.

The DMF was then removed at reduced pressure and the crude product was partitioned between H₂O and methylene chloride. The aqueous layer was extracted 3 times with methylene chloride and the combined organic fractions were filtered through MgSO₄ and concentrated at reduced pressure. The product was chromatographed (silica, 2:1 ether:hexanes) giving 8 gm of pure azide P.

m.p: 142°–143° C.

TLC (silica, 2:1 ether:hexanes): $R_f=0.45$.

An. Calc. for $C_{11}H_{12}N_4O.\frac{1}{4}H_2O$. N, 25.36; C, 59.79; H, 5.44. Found: N, 25.17; C, 59.37; H, 5.39.

NMR (CDCl₃, TMS): 1.6–2.9 (m, 6H); 3.4–3.7 (bt, 1H); 7.2 (s, 4H); 8.5 (bs, 1H);

mass spectrum: m/e 188, (M⁺—N₂); 159 (C=O).

C.
3-Azido-1-(t-butoxycarbonylmethyl)-hexahydrobenzoazocine-2-one

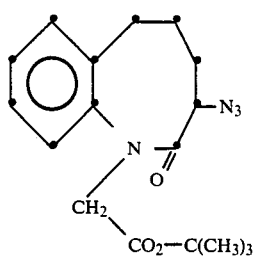

Q

To a suspension of 1.86 gm of sodium hydride (50% suspension, prewashed with hexanes) in 40 ml THF at 0° C. was added dropwise a solution of 8 gm (0.037 mol) of azide lactam and 5.63 ml of t-butyliodo acetate in 40 ml of THF. The reaction was found to be complete upon the completion of the addition. (TLC, silica gel, 2:1 ether:hexanes). The reaction mixture was then quenched by the addition of 20 ml of saturated NH₄Cl. The solution was extracted three times with 50 ml portions of ethyl acetate. The combined organic fractions were filtered through MgSO₄ and concentrated in vacuo. The crude product was purified by chromatography on silica gel using 2:1 ether:hexanes as eluant. The fractions containing the desired product were combined and concentrated at reduced pressure to give 11 gm of the desired product Q.

m.p.: 120°–121° C.

TLC (silica, 2:1 ether:hexanes): $R_f=0.75$.

NMR (CDCl₃, TMS): 1.5 (s, 9H); 1.9–3.0 (m, 6H); 3.35–3.6 (dd, 1H); 4.0–4.6 (AB, 2H); 7.2 (s, 4H).

An. Calc. for $C_{14}H_{22}N_4O_3.\frac{1}{2}H_2O$. N, 16.50; C, 60.11; H, 6.48. Found: N, 16.39; C, 60.29; H, 6.58.

mass spectrum: m/e 302, (M⁺—N₂); 257 (M⁺—OC₄H₉).

D.
3-Amino-1-(t-butoxycarbonylmethyl)-hexahydrobenzoazocine-2-one

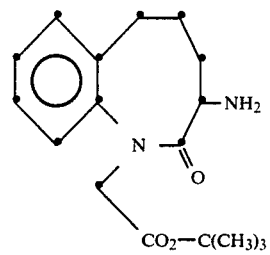

S

A solution of 9.5 gm (0.0287 mol) of azide lactam Q in 100 ml of absolute ethanol with 900 mg of 10% Pd/C was hydrogenated 12 hours at 40 lbs of hydrogen at room temperature. The reaction mixture was subsequently filtered and the filtrate concentrated in vacuo to give 98.7 gm of amine S.

NMR (CDCl₃, D₂O, TMS): 1.5 (s, 9H); 1.6–2.3 (m, 4H); 2.7–2.9 (t, 3H); 3.2–3.4 (m, 1H); 4.0–4.6 (ABQ, 2H); 7.2 (s, 4H).

E.
1-t-Butoxycarbonylmethyl-3-(1-carboethoxy-3-phenyl-1-propyl)aminohexahydrobenzazocine-2-one
(Racemate mixture)

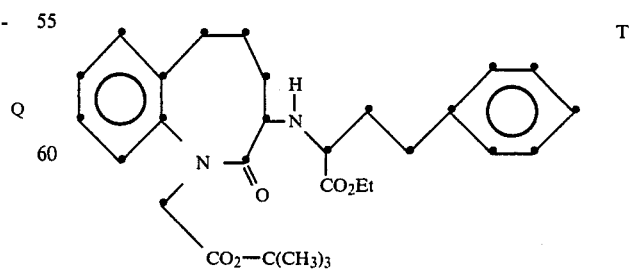

T

A solution of 2 gm (0.0066 mol) of the 3-amino-1-(t-butoxycarbonylmethyl)-hexahydrobenzoazocine-2-one, 6.7 gm of ethyl-4-phenyl-2-oxobutyrate and 377 ml of acetic acid in 20 ml of ethanol was stirred 1 hour at room temperature. To the stirring reaction mixture was slowly added over a period of 8 hours a solution of 1 gm of sodium cyano borohydride in 20 ml of ethanol. After stirring a further 8 hours the reaction was concentrated at reduced pressure and partitioned between water and ethyl acetate. After extracting twice with ethyl acetate the combined organic layers were filtered through MgSO$_4$ and concentrated in vacuo. the crude reaction mixture was chromatographed (silica, 7:3 hexanes:ethyl acetate) and two diastereomeric racemates of T were isolated.

Racemate diester A: 1.7 gm.

TLC (7:3 hexanes:ethyl acetate): R$_f$=0.39.

NMR (CDCl$_3$, TMS): 1.2 (+, 3H), 1.5 (s, 9H), 1.6–3.2 (m, 13H), 4.1 (Q, 2N), 4.3 (bs, 2H), 6.9–7.2 (m, 9H).

Racemate diester B: 1 gm.

TLC (7:3 hexanes:ethyl acetate): R$_f$=0.28.

NMR (CDCl$_3$, TMS): 1.1 (+, 3H), 1.5 (s, 9H), 1.6–3.2 (m, 13H), 3.9 (Q, 2N), 4.3 (bs, 2H), 7.0–7.2 (two overlapping bs, 9H).

EXAMPLE 9

1-Carboxymethyl-3-(1-carboxy-3-phenyl-1-propyl-)aminohexahydrobenzoazocine-2-one

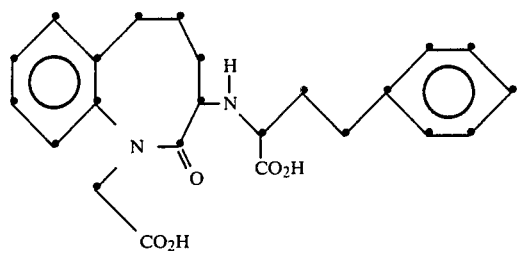

U

Racemate A

The racemate A diester of Example 8, (1.7 gm (0.0035 mol) was stirred 1 hour at room temperature with 5 ml of trifluoroacetic acid at which time the reaction mixture was concentrated at reduced pressure. To the crude product in 7 ml of methanol was added 3.5 ml of a 4N solution of sodium hydroxide in water stirring continued overnight at room temperature. The reaction mixture was subsequently applied to a column of Dowex 50 (H+) and eluted first with H$_2$O and then with 5% pyridine. The appropriate pyridine fractions were concentrated giving 600 mg of the diacid U racemate A.

An. Calc. for C$_{23}$H$_{26}$N$_2$O$_5$·½H$_2$O. C, 65.80; H, 6.19; N, 6.67. Found: C, 66.01; H, 6.32; N, 6.65.

NMR (D$_2$O=4.6): 1.5–3.2 (m, 12H), 4.1 (s, 2H), 6.8–7.2 (m, 9H).

Racemate B

The racemate B diester of Example 8 (1 gm, 0.002 mol) was converted to 500 mg of the diacid U by the same procedure as described above.

An. Calc. for C$_{23}$H$_{26}$N$_2$O$_5$·½H$_2$O. N, 6.67; C, 65.80; H, 6.19. Found: N, 6.62; C, 66.07; H, 6.27.

NMR (D$_2$O=4.9): 1.6–3.4 (m, 12H), 4.2 (6s, 2H), 7.2–7.5 (m, 9H).

EXAMPLE 10

1-Carboethoxymethyl-3-(1-carboethoxy-3-phenyl-1-propyl)-amino homodihydrocarbostyril (Racemate A)

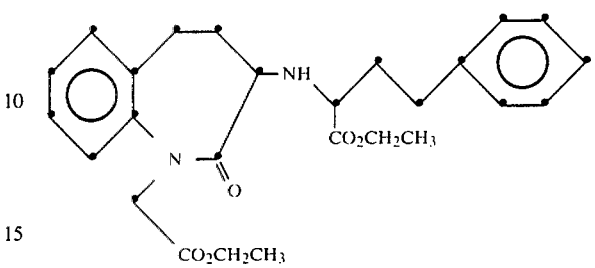

A solution of 100 mg of 1-t-butoxycarbonylmethyl-3-(1-carboethoxy-3-phenyl-1-propyl)amino homodihydrocarbostyril (racemate A of Example 3) in 20 ml of ethanol was saturated with HCl gas, sealed and stirred overnight at room temperature. The reaction mixture was concentrated in vacuo and partitioned between ethylacetate and a saturated solution of K$_2$CO$_3$ in H$_2$O. The H$_2$O layer was extracted 2 times with ethyl acetate, filtered through MgSO$_4$ and concentrated at reduced pressure. The crude reaction product was chromatographed (silica, 2:1, ethylacetate:hexanes) to give 85 mg of product.

TLC (silica, 3:1 ether:hexanes): R$_f$=0.60.

NMR (CDCl$_3$, TMS): 1.1–1.5 (2t, 6H); 1.8–3.2 (m, 11H); 3.9–4.3 (2g, 4H), 4.1–4.7 (ABq, 2H), 17.1–17.3 (m, 9H).

EXAMPLE 11

1-Benzyloxy-3-(1-carboethoxy-3-phenyl-1-propyl-)amino homodihydrocarbostyril

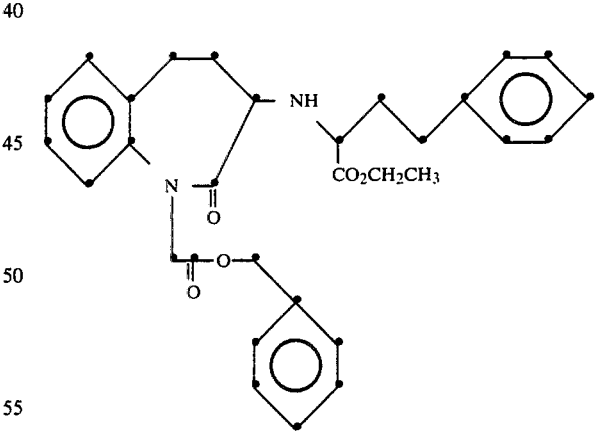

To a solution of 200 mg of the monobenzylester M (Example 7) in 5 ml of methylene chloride at 0° C. was added a solution of diazoethane in ether until TLC indicated reaction was complete. The reaction mixture was concentrated at reduced pressure and chromatographed (silica, 3:2, hexane:ethylacetate) to give 75 mg of the title diester product.

TLC (silica, 3:2, hexane:ethylacetate): R$_p$=0.50.

NMR: (1.2 (t, 3H), 1.6–3.4 (m, 11H); 4.1 (9, 2H); 4.5 (ABq, 2H), 5.1 (s, 2H), 7.0–7.3 (m, 14H).

EXAMPLE 12

1-t-Butoxycarbonylmethyl-3-(1-carboethoxy-3-(3)indo-lyl-1-propyl)amino homodihydrocarbostyril (Racemate Mixture)

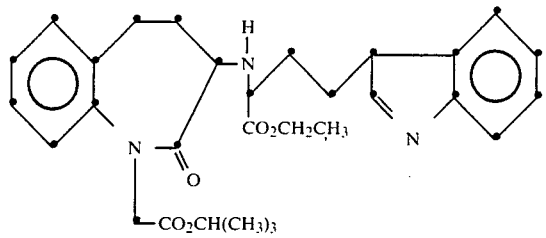

A solution of 0.7 gm of 1-t-butoxycarbonylmethyl-3-amino homodihydrocarbostyril (Compound D, Example 3), 0.6 gm of ethyl-4-(β-indolyl)-2-oxobutyrate and 0.27 ml of acetic acid in 10 ml of absolute ethanol was stirred 1 hour at room temperature. To the stirred solution was added dropwise over a 7 hour period a solution of 0.38 gm of NaCNBH₃ in 10 ml of ethanol. Aftre stirring a further 12 hours, the reaction was concentrated at reduced pressure and partitioned between H₂O and ethyl acetate. After extracting twice with ethylacetate, the combined organic layers were filtered through MgSO₄, concentrated in vacuo and chromatographed (silica, 1:1, ethylacetate:hexane) to afford two diasteriomeric racemates.

Racemate A: 170 mg.
TLC (silica, 1:1, ethylacetate:hexane): $R_f=0.52$.
NMR (CDCl₃, TMS): 1.2 (t, 3H); 1.4 (s, 9H); 1.7–3.6 (m, 11H); 4.1 (9, 2H); 4.4 (ABq, 2H); 6.7–7.4 (m, 9H); 8.2 (bs, 1H).
mass spectrum: M+ 519.

Racemate B: 200 mg.
TLC (silica, 1:1, ethylacetate:hexane): $R_f=0.39$.
NMR (CDCl₃, TMS): 1.1 (t, 3H); 1.4 (s, 9H); 1.8–3.5 (m, 11H); 4.0 (9, 2H); 4.45 (ABq, 2H); 6.9–7.6 (m, 9H); 8.4 (bs, 1H).
mass spectrum: M+ 519.

EXAMPLE 13

1-Carbomethoxymethyl-3-(1-carbomethoxy-3-phenyl-1-propyl)aminohexahydrobenzoazocine-2-one

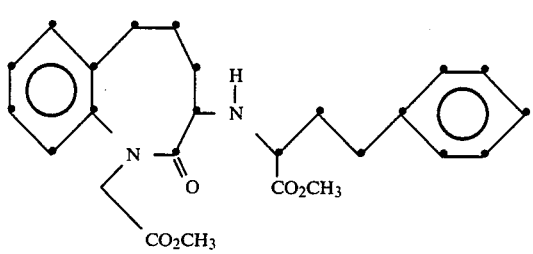

The dimethyl ester W can be prepared from 1-carboxymethyl-3-(1-carboxy-3-phenyl-1-propyl)aminohexahydrobenzoazocine-2-one using a process analogous to that described in Example 5.

EXAMPLE 14

1-Carboxymethyl-3-(1-carboethoxy-3-phenyl-1-propyl)aminohexahydrobenzoazocine-2-one

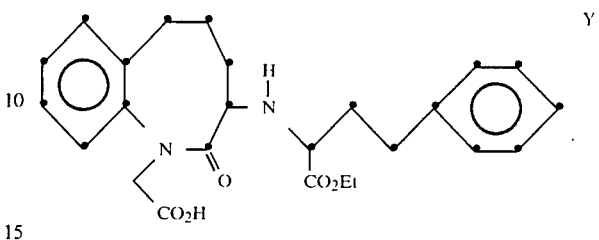

The mono ethyl ester Y can be obtained from the t-butyl/ethyl diester (Racemate B of Example 9) by treatment with trifluoroacetic acid as in the analogous homodihydrocarbostyril Example 6.

EXAMPLE 15

1-Carbobenzyloxymethyl-3-(1-carboxy-3-phenyl-1-propyl)aminohexahydrobenzoazocine-2-one

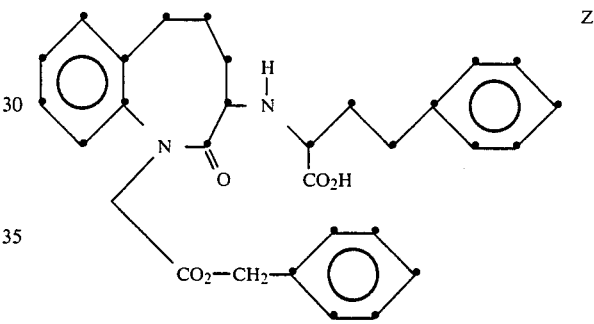

The mono benzyl ester Z may be prepared from 3-amino hexahydrobenzoazocine by a sequence analogous to that described in Example 7.

Examples of the various keto acids and keto esters having the formula:

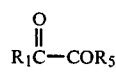

which can be employed in the processes described above to prepare compounds of Formula I are illustrated below in Table I.

TABLE I

Keto Acids and Esters of the Formula $R_1C-COR_5$ ‖ O (a)
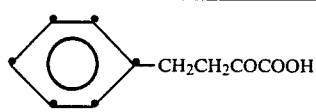

(b)
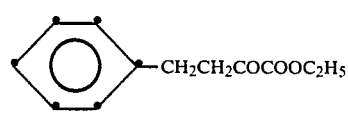

TABLE I-continued

Keto Acids and Esters of the Formula $R_1C\text{—}COR_5$ with $\|$ O (c) ⬡—CH$_2$CH$_2$COCOOCH$_2$C$_6$H$_5$ (d) ⬡—CH$_2$CH$_2$CH$_2$COCOOC$_2$H$_5$ (e) Cl—⬡—CH$_2$COCOOH (f) indole—CH$_2$CH$_2$COCOOC$_2$H$_5$ (with NH)

(g) thiophene—CH$_2$CH$_2$COCOOH (h) pyridine—CH$_2$CH$_2$COCOOC$_2$H$_5$ (i) quinoline—CH$_2$CH$_2$COCOOH (j) HO—⬡—CH$_2$CH$_2$COCOOH (k) Cl (on ring)—⬡—CH$_2$CH$_2$COCOOH (l) O$_2$N (on ring)—⬡—CH$_2$CH$_2$COCOOC$_2$H$_5$
(precursor for the corresponding amino compound)

(m) CH$_2$NH—CBZ (on ring)—⬡—CH$_2$CH$_2$COCOOH
(precursor for the corresponding amino compound)

(n) ⬡—O—CH$_2$COCOOC$_2$H$_5$ (o) ⬡—S—CH$_2$COCOOC$_2$H$_5$

Additional examples of the compounds of Formula I which can be synthesized by the procedures described herein are illustrated by, but not limited to, the compounds illustrated in Table II below:

TABLE II
Additional Examples of Compounds of Formula I

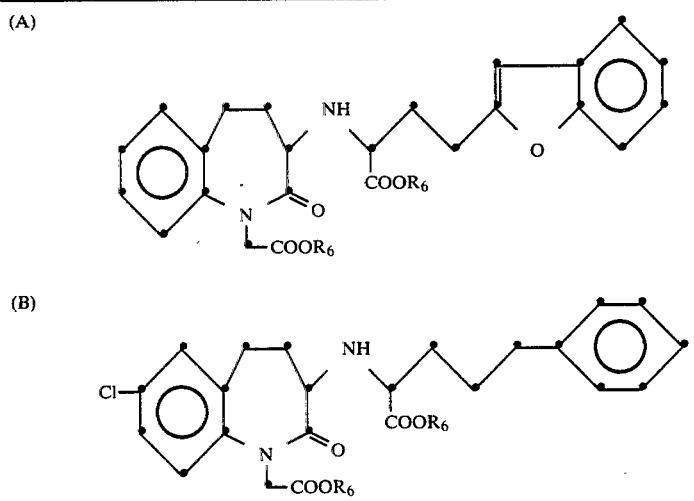

(A)

(B)

TABLE II-continued
Additional Examples of Compounds of Formula I
(C) 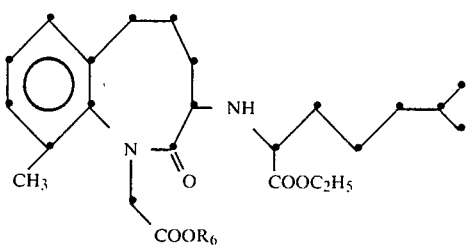
(D) 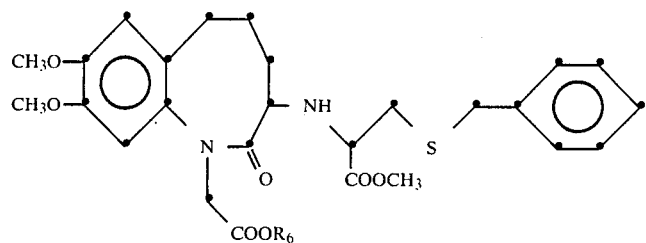
(E) 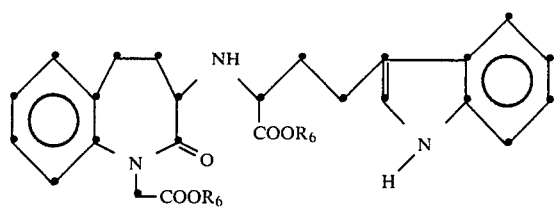
(F) 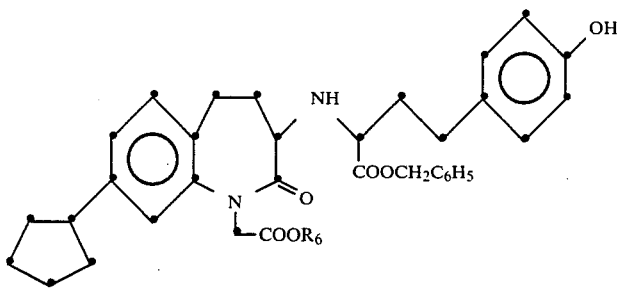
(G) 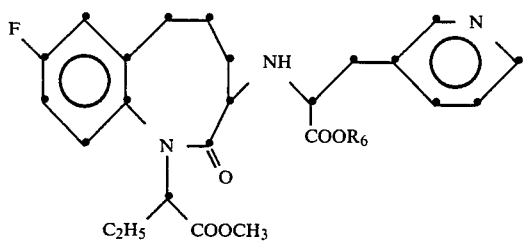
(H) 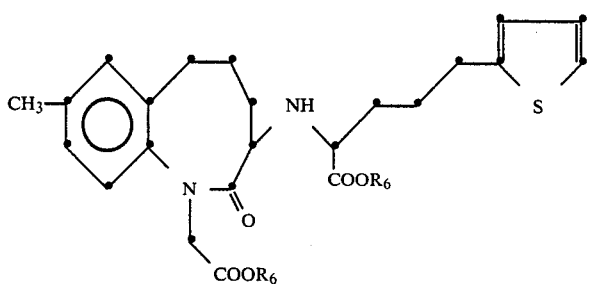

TABLE II-continued
Additional Examples of Compounds of Formula 1

(I)
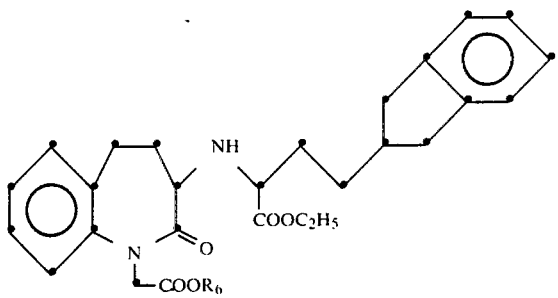

(J)
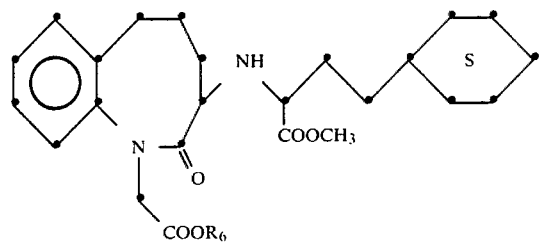

What is claimed is:

1. A method of treating gastrointestinal disorders, central nervous system disorders, or regulating appetite in mammals which comprises administering to a patient in need of such treatment a pharmaceutically effective amount of a compound having the formula:

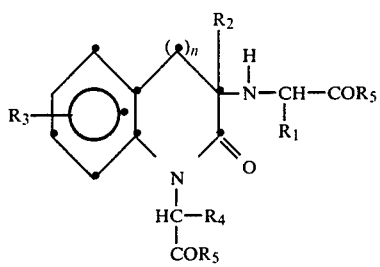

wherein
n is 1, 2 or 3,
$R_4$ is hydrogen, ower alkyl, aryl;
$R_2$ is hydrogen,
$R_3$ is H, halo, lower alkyl, lowercycloalkyl, or loweralkoxy,
$R_1$ is
hydrogen;
alkyl of from 1 to 12 carbon atoms; cycloalkyl of from 5 to 8 methylene groups; alkenyl or 2 to 12 carbon atoms; alkynyl or 2 to 12 carbon atoms;
substituted loweralkyl wherein the substituent can be halo, hydroxy, carboxy, carboxamido, loweralkylthio, loweralkoxy, loweralkoxycarbonyl, loweraralkoxycarbonyl, amino, loweralkylamino, lowerdialkylamino, acylamino;
substituted loweralkylamino wherein the substituent can be halo, hydroxy, alkoxy or cyano; arloweralkylamino; aryloxy; arylthio; aralkyloxy; aralkylthio; benzofused cycloalkyl or bicycloalkyl of from 8-12 carbon atoms;
aryl or heteroaryl which may be mono-, di- or tri-substituted by loweralkyl, hydroxy, loweralkoxy, halo, amino, acylamino, loweralkylthio or aminoloweralkyl;
benzofused cycloalkyl or bicycloalkyl of from 8 to 12 carbon atoms;
arloweralkyl, arloweralkenyl, heteroarylloweralkyl and heteroarylloweralkenyl in which the aryl or heteroaryl rings may be mono-, di- or tri-substituted by halo, loweralkyl, hydroxy, loweralkoxy, amino, loweralkylamino, diloweralkylamino, aminoloweralkyl, acylamino, carboxy, halolower-alkyl, nitor, cyano or sulfonamido; aralkyl or heteroaralkyl which include branched loweralkyl groups;
substituted aralkyl or substituted heteroaralkyl which include branched loweralkyl groups wherein the loweralkyl groups can be substituted by amino, acylamino, or hydroxyl and the aryl and heteroaryl groups can be substituted by halo, dihalo, loweralkyl, hydroxy, loweralkoxy, aryloxy, aroyl, arylthio, amino, aminoloweralkyl, loweralkanoylamino, aroylamino, lowerdialkylamino, loweralkylamino, hydroxy, hydroxyloweralkyl, trihaloloweralkyl, nitro, cyano, or sulfonamido;
any of the arloweralkyl or alkenyl and heteroloweralkyl or alkenyl groups described above in which the aryl or heteroaryl ring is partially or completely hydrogenated; substituted loweralkyl having the formula $R_A{}^1(CH_2)_n$—Q—$(CH_2)_m$ wherein n is 0-2, n is 1-3, $R_A{}^1$ is aryl or heteroaryl optionally substituted by amino, lower-dialkylamino, loweralkylamino, hydroxy, hydroxyloweralkyl, aminoloweralkyl, trihaloloweralkyl, cyano, nitro, sulfonamido, aroyl, loweralkyl, halo, dihalo, and loweralkoxy, and Q is O, S, SO, $SO_2$, N—$R_B{}^1$, $CONR_C{}^1$, $NR_C{}^1CO$, CH=CH wherein $R_B{}^1$ is hydrogen, loweralkyl, aryl, aralkyl, loweralkanoyl, or aroyl, and $R_C{}^1$ is hydrogen, or loweralkyl;
$R_5$ is
—$OR_6$ or —$NR_7R_8$ wherein $R_6$, $R_7$ and $R_8$ are independently selected from hydrogen;
lower alkyl;

substituted lower alkyl wherein the substituents are monohydrozy, dihydroxy or acylamino;
acylloweralkyl;
carboxyloweralkyl;
carboxamidoloweralkyl;
arloweralkyl;
aryl;
heteroaryl and heteroaralkyl;
wherein aryl is selected from the group consisting of unsubstitued phenyl, unsubstituted napthyl and unsubstituted biphenyl; acyl represents loweralkanoyl and aroyl; heteroaryl is selected from the group consisting of pyridyl, thienyl, furyl, imidazolyl, thiazolyl, indolyl, quinolinyl, isoquinolinyl, benzimidazolyl, benzothiazoly, benzthienyl and naphthyridyl; and, the pharmaceutically acceptable salts thereof.

2. The method of claim 1 wherein in said compound:
$n$ is 1, 2 or 3,
$R_4$ is hydrogen, lower alkyl, aryl;
$R_2$ is hydrogen,
$R_3$ is H, halo lower alkyl, or loweralkoxy,
$R_1$ is
  hydrogen;
  alkyl of from 1 to 12 carbon atoms; cycloalkyl of from 5 to 8 methylene groups; alkenyl of 2 to 12 carbon atoms; alkynyl of 2 to 12 carbons;
  substituted loweralkyl wherein the substituent can be halo, hydroxy, carboxy, carboxamido, loweralkylthio, loweralkoxy, loweralkoxycarbonyl, loweraralkoxycarbonyl, amino, loweralkylamino, lowerdialkylamino, acylamino;
  substituted loweralkylamino wherein the substituent can be halo, hydroxy, alkoxy or cyano; arloweralkylamino; aryloxy; arylthio; aralkyloxy; aralkylthio; benzofused cycloalkyl or bicycloalkyl of from 8–12 carbon atoms;
  aryl or heteroaryl which may be mono-, di- or tri-substituted by loweralkyl, hydroxy, loweralkoxy, halo, amino, acylamino, loweralkylthio or aminoloweralkyl;
  benzofused cycloalkyl or bicycloalkyl of from 8 to 12 carbon atoms;
  arloweralkyl, arloweralkenyl, heteroaryloweralkyl and heteroaryloweralkenyl in which the aryl or heteroaryl rings may be mono-, di- or tri-substituted by halo, loweralkyl, hydroxy, loweralkoxy, amino, loweralkylamino, diloweralkylamino, aminoloweralkyl, acylamino, carboxy, haloloweralkyl, nitor, cyano or sulfonamido; aralkyl or heteroaralkyl which include branched loweralkyl groups;
  substituted aralkyl or substituted heteroaralkyl which include branched loweralkyl groups wherein the loweralkyl groups can be substituted by amino, acylamino, or hydroxyl and the aryl and heteroaryl groups can be substituted by halo, dihalo, loweralkyl, hydroxy, loweralkoxy, aryloxy, aroyl, arylthio, amino, aminoloweralkyl, loweralkanoylamino, aroylamino, lowerdialkylamino, loweralkylamino, hydroxy, hydroxyloweralkyl, trihaloloweralkyl, nitro, cyano, or sulfonamido; any of the arloweralkyl or alkenyl and heteroloweralkyl or alkenyl groups described above in which the aryl or heteroaryl ring is partially or completely hydrogenated;
  substituted loweralkyl having the formula $R_A{}^1(CH_2)_n-Q-(CH_2)_m$ wherein n is 0–2, m is 1–3, $R_A{}^1$ is aryl or heteroaryl optionally substituted by amino, lower-dialkylamino, loweralkylamino, hydroxy, hydroxyloweralkyl, aminoloweralkyl, trihaloloweralkyl, cyano, nitoro, sulfonamido, aroyl, loweralkyl, halo, dihalo, and loweralkoxy, and Q is O, S, SO, $SO_2$, N—$R_B{}^1$, $CONR_C{}^1$, $NR_C{}^1CO$, CH=CH wherein $R_B{}^1$ is hydrogen, loweralkyl, aryl, aralkyl, loweralkanoyl, or aroyl, and $R_C{}^1$ is hydrogen, or loweralkyl;
$R_5$ is
  —$OR_6$ or —$NR_7R_8$ wherein $R_6$, $R_7$ and $R_8$ are independently selected from hydrogen;
  lower alkyl;
  substituted lower alkyl wherein the substituents are monohydroxy, dihydroxy or acylamino;
  acylloweralkyl;
  arloweralkyl;
  carboxyloweralkyl;
  carboxamidoloweralkyl;
  aryl;
  heteroaryl and heteroaralkyl;
wherein aryl is selected from the group consisting of unsubstituted phenyl, unsubstituted naphyl and unsubstituted biphenyl; acyl represents loweralkanoyl and aroyl; heteroaryl is selected from the group consisting of pyridyl, thienyl, furyl, imidazolyl, thiazolyl, indolyl, quinolinyl, isoquinolinyl, benzimidazolyl, benzothiazolyl, benzthienyl and naphthyridyl.

3. The method of claim 2 wherein said compound is a member of the group:
1-t-butoxycarbonylmethyl-3-(1-carboethoxy-3-phenyl-1-propyl)amino homodihydrocarbostyril;
1-carbomethoxymethyl-3-(1-carbomethoxy-3-phenyl-1-propyl)amino homodihydrocarbostyril;
1-t-butoxycarbonylmethyl-3-(1-carboethoxy-3-phenyl-1-propyl)amino hexahydrobenzazocine-2-one;
1-benzyloxycarbonylmethyl-3-(1-carboethoxy-3-phenyl-1-propyl)amino homodihydrocarbostyril;
1-carboethoxymethyl-3-(1-carboethoxy-3-phenyl-1-propyl)amino homodihydrocarbostyril;
1-t-butoxycarbonylmethyl-3-(1-carboethoxy-3-(3-indolyl)-1-propyl)amino homodihydrocarbostyril; and,
1-carboxymethyl-3-(1-carboethoxy-3-phenyl-1-propyl)amino homodihydrocarbostyril.

* * * * *